United States Patent [19]

Parisi et al.

[11] Patent Number: 4,886,491

[45] Date of Patent: Dec. 12, 1989

[54] LIPOSUCTION PROCEDURE WITH ULTRASONIC PROBE

[76] Inventors: Tulio Parisi, 9011 Mesa Woods Ave., San Diego, Calif. 92126; Richard K. Massengill, 15350 Via Molinero, Poway, Calif. 92064

[21] Appl. No.: 161,796

[22] Filed: Feb. 29, 1988

[51] Int. Cl.[4] ............................................. A61B 17/20
[52] U.S. Cl. .................................... 604/22; 604/902; 128/303 R
[58] Field of Search .............. 604/22, 902; 128/303 R

[56] References Cited

U.S. PATENT DOCUMENTS

| | | | |
|---|---|---|---|
| 4,040,414 | 8/1977 | Suroff | 604/22 |
| 4,136,700 | 1/1979 | Broadwin et al. | 128/305 |
| 4,169,984 | 10/1979 | Parisi | 128/24 A |
| 4,515,583 | 5/1985 | Sorich | 604/22 |
| 4,531,934 | 7/1985 | Kossovsky et al. | 604/22 |
| 4,735,605 | 9/1986 | Swartz | 604/22 |

OTHER PUBLICATIONS

"Body Sculpturing", Clinics in Plastic Surgery, Baroudi, M. D., vol. 11, No. 3, Jul. 1984, pp. 419–443.
"Body Contouring with Suction Lipatomy", Clinics in Plastic Surgery, Kesselring, M.D., vol. 11, No. 3, Jul. 1984, pp. 393–408.
"Percutaneous Ultrasonic Lithotripsy" (p. 430).
"The Cavitron Ultrasonic Aspirator in Tumor Surgery", (Epstein, p. 499).

Primary Examiner—Jerome L. Kruter
Attorney, Agent, or Firm—King and Schickli

[57] ABSTRACT

A method of removing human body fatty tissue includes inserting an ultrasonic aspirating probe into the body in the area of the fatty tissue between the flesh, including blood vessels and arteries, and the muscle. The probe is ultrasonically vibrated at high frequencies and low amplitudes creating localized tissue separation and frictional heat. This heat causes the fatty tissue surrounding the probe to melt. The probe is specially adapted to provide a localized flow of irrigating fluid. This fluid serves to emulsify the melted and separated fat. The emulsified fat is then aspirated through specially designed orifices from the body using suction.

7 Claims, 2 Drawing Sheets

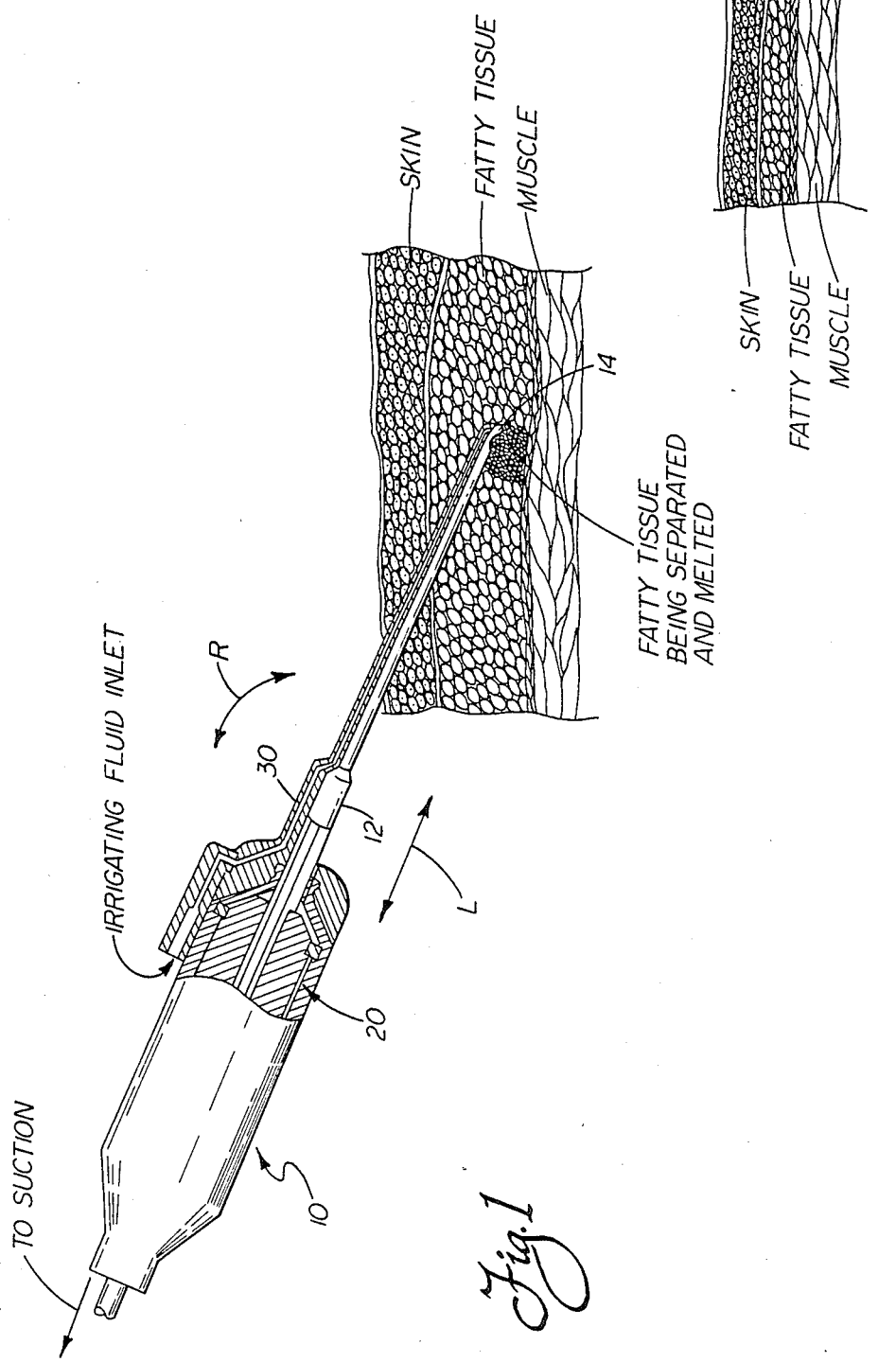

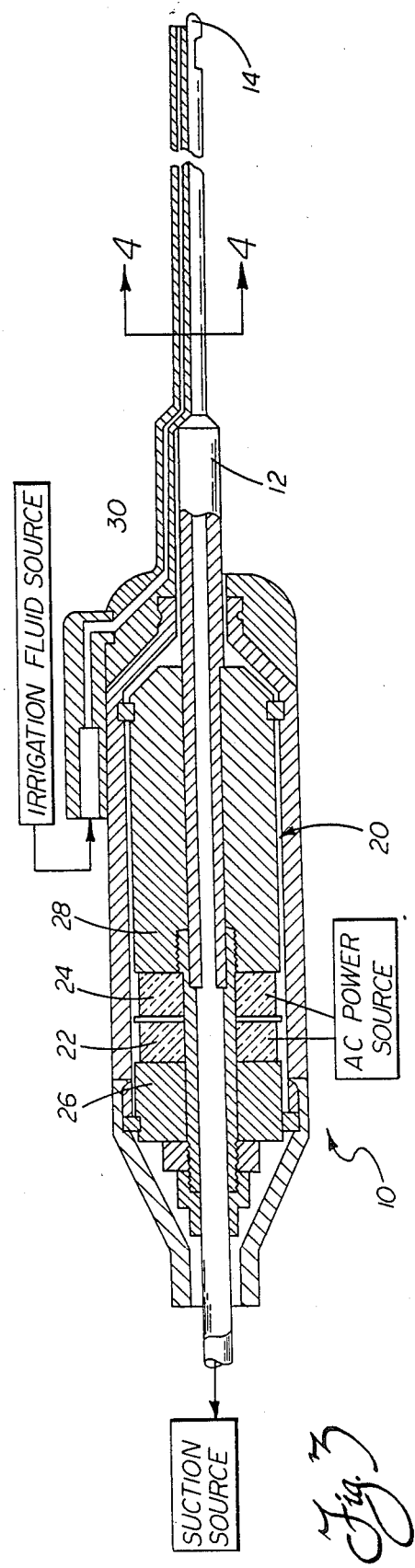
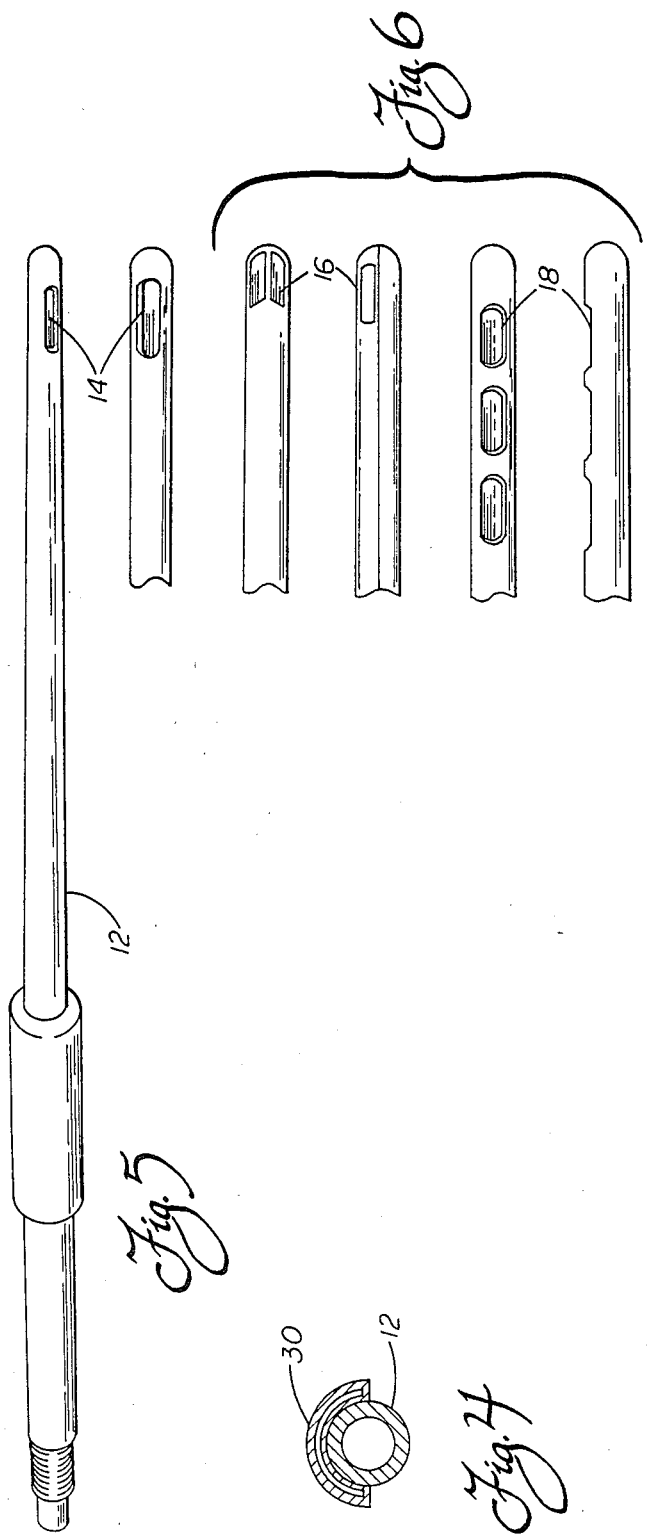

LIPOSUCTION PROCEDURE WITH ULTRASONIC PROBE

TECHNICAL FIELD

The present invention relates generally to surgical methods of removing tissue, and more particularly to a method of in vivo ultrasonic removal of animal fatty tissue.

BACKGROUND OF THE INVENTION

This invention concerns a method of liposuction. Liposuction is a type of cosmetic surgery whereby undesirable accumulations of body fat are removed by suction. Liposuction is becoming increasingly popular, and is seen by many as a way to quickly remove undesirable body fat which may or may not be removed by the more traditional ways of diet and exercise.

The traditional liposuction techniques include the use of a cannula connected to an external source of suction. In use, an incision is made in the area of the fat desired to be removed, the cannula inserted in the area (between the flesh and muscle), and the suction begun. The fat is then sucked out of the body. This basic method has its disadvantages, however, because the fat is relatively difficult to separate from the surrounding tissue by simply the sucking action. There is a tendency for the entry orifice on the cannula to clog with the fat. In other words, it is difficult to keep the operation going without stopping to clean out the cannula orifice. Normally, the surgeon attempts to compensate for this problem by manually moving the cannula within the cavity, and even periodically withdrawing it to force the fat that is stuck in the orifice. Further, the surgeon must be careful not to allow the suction to pull and remove desirable tissues, such as the flesh, muscle, blood vessels and the like. Therefore, the speed, safety and effectiveness of the current liposuction method leaves much to be desired and a successful operation depends on the practitioner's exceptional skill.

It is known to use ultrasonically vibrating/aspirating probes in the fields of cataract surgery and dental cleaning. There have also been suggestions of use of these probes in removing other types of relatively hard body tissues, such as brain tumors.

In each case, the intent is to introduce the vibrating probe into the area of material desired to be removed, and use the ultrasonic vibrations to physically fracture or cut the material. Such a procedure lends itself well to cataract surgery, for example, because the cataract desired to be removed is relatively hard and capable of being fractured.

Representative patents in this field include my own prior U.S. Pat. No. 4,169,984, issued Oct. 2, 1979. Also, U.S. Pat. No. 4,515,583 assigned to Cooper Laser-Sonics, Inc. and U.S. Pat. No. 4,531,934 to Kossovsky et al teach the same basic approach and limitations. In other words, these patents teach an ultrasonic surgical probe with aspirator used to fragment and remove undesirable cataract or other hard tissue. Use of ultrasonics in cataract surgery is, in fact, widely regarded as safe and effective.

A need exists for a method of performing liposuction which removes the unwanted relatively soft, fatty tissue in much the same manner as utilizing the cannula, yet which is more effective and may be carried out without interruption. Such a method would greatly assist those practicing liposuction to more quickly and reliably remove unwanted fatty tissue.

SUMMARY OF THE INVENTION

Accordingly, it is an object of the present invention to provide a method for aspirating animal fatty tissue utilizing an ultrasonic probe.

Another object of the present invention is to provide a method for aspirating animal fatty tissue by emulsifying the tissue and then removing it by use of an externally provided suction.

Still another object of the present invention is to provide a method for aspirating animal fatty tissue without damage to or removal of flesh tissue, blood vessels, and the like.

Yet another object of the present invention is to provide a method for aspirating animal fatty tissue utilizing ultrasonic vibrations to create more efficient tissue separation, and even localized tissue melting through frictional heat, thereby allowing highly efficient removal.

Additional objects, advantages and novel features of the invention will be set forth in part in the description which follows, and in part, will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention as described herein, a method is provided to perform a liposuction procedure utilizing an ultrasonic probe. It should be recognized that although this method can be used on all animals, it is intended to be utilized primarily on humans. Liposuction is a type of cosmetic surgery wherein undesirable fatty tissue is removed from the body. This is usually done y using a non-vibrating cannula connected to an external suction source.

Liposuction is rapidly gaining popularity because it provides an easy way to remove unwanted body fat. Generally, dieting serves only to reduce the size of fat cells, not their number. It is this fact which makes maintaining one's lowered body weight after dieting so difficult. Liposuction takes an alternative approach by physically removing the fat cells. Additionally, liposuction serves as a means for reducing the bulk in areas which could not be reduced by dieting and exercise. For example, it is not unusual to perform liposuction on an individual's eyelids or under the eyes, and at other localized areas on the face.

The method of the present invention provides for inserting the tip of an ultrasonic aspirating probe into the area of the fatty tissue. One such probe, which can be readily modified for this procedure, is my prior art probe as disclosed in U.S. Pat. No. 4,169,984 and mentioned above. The probe includes a housing containing an internal piezoelectric crystal transducer assembly for creating ultrasonic vibration. A hollow insert with a probe tip is threadedly engaged in the transducer assembly of the probe.

To perform the method of the present invention, the probe tip is what must be modified. The choice of the tip depends upon the precise nature of the liposuction procedure being performed. Several alternative tips are illustrated and a selection is made based on the particular type of body area being treated. A rounded, bullet-shaped tip with a closed end and a single elongated entry orifice is the standard configuration and may be used for a majority of body areas. A tip with a portion of the end open is utilized for localized entry and fat removal, such as in areas around the smaller body appendages; whereas, a tip having multiple entry orifices is provided for unobstructed and flatter areas, such as the thighs and buttocks where the probe tip may be extended into the fatty area for a substantial distance.

Additionally, an irrigation sleeve is provided which partially surrounds the probe tip and provides a localized flow of irrigating solution to the body cavity where the fat is being removed. The irrigation sleeve snaps onto the probe and is readily removable.

In an alternative method, the irrigating solution is introduced directly through the probe tip. Obviously, in this alternative method, the probe operates by cycling between aspirating and irrigating modes. The choice of which method to use depends on the type and location of the operation being performed.

During operation, the surgeon determines the location and extent of fatty tissue to be removed. An incision is made large enough to permit passage of the probe tip. The tip is guided through the skin and flesh layers, which include the blood vessels, and into the layer of fatty tissue below.

In the preferred method, the probe tip is vibrated at 40,000 cycles per second at an amplitude of 2 mil. This high frequency, low amplitude vibration serves to efficiently and safely separate the fatty tissue and create localized heat through frictional contact. This localized frictional heat serves to assist in the removal by physically melting a thin layer of surrounding fatty tissue.

The separated and melted fatty tissue is emulsified in the preferred embodiment by application of the saline irrigating solution from the tip of the irrigation sleeve. The emulsified solution is then aspirated by use of an external suction. It should be pointed out that the intensity of the vibration and localized heat applied can be varied by adjusting the frequencies and amplitudes of vibration.

The method of the present invention results in liposuction procedures significantly more reliable than were possible using the traditional non-vibrating cannula method. This is because the ultrasonic probe tip operating in this manner does not disturb any of the surrounding tissue with which it comes into contact. By removing only the fatty tissue and leaving the other tissue including the blood vessels intact, a safer surgical procedure results. As a result, healing time is also significantly reduced.

Still other objects of the present invention will become apparent to those skilled in this art from the following description wherein there is shown and described a preferred embodiment of this invention, simply by way of illustration of one of the modes best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification, illustrates several aspects of the present invention and together with the description serves to explain the principles of the invention. In the drawing:

FIG. 1 is a cut-away view of an ultrasonic aspirating probe shown inserted into the fatty tissue cavity of a body between the skin/flesh layers and the muscle layer and performing the method of the invention;

FIG. 2 is a cross-sectional view of the area of the body as shown in FIG. 1 with the fat having been removed by the method to form a slimmer profile;

FIG. 3 is a cut-away view of a complete ultrasonic probe suitable for use in carrying out the method and additionally including an irrigation sleeve;

FIG. 4 is a cross-sectional view taken along section line 4—4 of FIG. 3;

FIG. 5 is a perspective view of a preferred, general purpose insert for use with the probe of FIG. 4 to perform the method of the present invention and with an extra detailed plan view of the tip illustrating the entry orifice; and FIG. 6 is a composite showing of two additional tips, including for each a plan and side view illustrating alternative orifice configurations.

Reference will now be made in detail to the present preferred method of the invention, an example of which is illustrated in the accompanying drawing.

DETAILED DESCRIPTION OF THE INVENTION

Reference is now made to FIGS. 1 and 3 showing an ultrasonic aspirating probe 10 ideally suited for carrying out the method of the present invention. The probe 10 includes a hollow insert 12 having a probe tip 14. The probe 10 further includes an internal ultrasonic transducer assembly 20. Assembly 20 includes piezoelectric crystals 22, 24 which are securely retained within body members 26, 28. As is known in the art, an alternating voltage of ultrasonic frequency is applied to the transducer assembly 20. This causes the crystals 22, 24 to vibrate ultrasonically. This vibration is transferred to the hollow insert 12 and the probe tip 14. For a more detailed review of the transducer assembly and how it operates to produce ultrasonic vibration, reference is made to my prior U.S. Pat. No. 4,169,984, mentioned above and which is incorporated herein by reference.

To perform the method of the present invention, the probe tip 14 must be modified from the probe tips commonly known and used by practitioners of the liposuction art. As shown in FIGS. 5 and 6, various probe tips 14, 16 and 18 are provided, the choice of which depends upon the precise nature of the liposuction procedure being performed. More specifically, the choice of which tip 14, 16 or 18 to use depends upon the particular type of body area being treated. FIG. 5 shows an insert 12 having a rounded bullet-shaped tip 14. This tip further includes a closed end and a single elongated entry orifice. From my experimentation, I have established this probe tip 14 as the standard configuration, and it is used for the majority of body areas.

FIG. 6 shows two alternative probe tip configurations. Probe tip 16 is a bullet-shaped tip having a portion of the end open. Probe tip 16 is used to remove fat in tight areas, such as around the small appendages of the body. Probe tip 18 having multiple entry orifices is used in body areas providing clear access over a wider area. Thus, probe tip 18 is particularly useful in areas, such as the thighs buttocks where the probe tip 18 may be extended into the fatty area for a substantial distance. This allows faster fatty tissue removal, resulting in quicker, more efficient liposuction operations.

Irrigation sleeve 30 is provided to direct a flow of irrigating solution directly to the probe tip 14 (see FIGS. 3 and 4). Sleeve 30 partially surrounds the insert 12 including probe tip 14. Advantageously, sleeve 30 snaps onto probe 10 and is readily removable. Because sleeve 30 is non-vibrating and closely surrounds the insert 12 (see FIG. 4), sleeve 30 serves as a thermal insulator. In other words, the tissues found in the areas above the sleeve 30 are protected from the ultrasonically created heat. In this way, the ultrasonic liposuction may be performed in areas very close to the skin, without damaging this delicate tissue.

During operation, the surgeon determines the location and extent of fatty tissue to be removed. Based on this initial determination, the surgeon next chooses, and installs within probe 10, the hollow insert 12 having the appropriate probe tip 14, 16 or 18. An incision is made, and the tip 14, 16 or 18 is guided through the skin and flesh layers, which include the blood vessels, and into the layer of fatty tissue below.

In the preferred method, the probe 10 is vibrated at approximately 40,000 cycles per second at an amplitude of about 2 mil. This high frequency, low amplitude vibration serves to efficiently and safely separate the fatty tissue and create localized heat through frictional contact. Advantageously, this localized frictional heat serves to assist in the removal by physically melting a thin layer of surrounding fatty tissue.

During use, and as shown in FIG. 1, the probe 10 is moved in a back and forth and twisting manner as is shown by action arrows L and R respectively. This motion helps to further separate the fatty tissue, and generally speeds up the operation.

The separated and melted fatty tissue is emulsified in the preferred embodiment by application of a saline irrigating solution from the tip of irrigating sleeve 30. The emulsified solution is then aspirated by use of an external suction source. The intensity of the vibration and localized heat applied can be varied by adjusting the frequencies and amplitudes of ultrasonic vibration. This allows the surgeon to fine tune the liposuction procedure to each individual situation.

As shown in FIG. 2, using the method of the present invention removes the fatty tissue and its associated bulk, leaving the desired thinner profile appearance. The choice of how much fatty tissue to remove depends on the final appearance desired by the patient. The surgeon can remove as little, or as much fatty tissue as necessary, to achieve the desired final appearance.

The method of the present invention results in liposuction procedures significantly more reliable than were possible using the traditional non-vibrating cannula method. This is because the ultrasonic probe 10 aspirates only the undesirable fatty tissue while leaving the desirable tissue such as blood vessels, muscle and the like intact. Advantageously, this provides a safer surgical procedure characterized by reduced healing times.

The vibration constantly and effectively shakes the separated fatty tissues at the entry orifice(s) to allow easier entry into the tip 14, 16 or 18 and prevent clogging. In this manner the process is substantially accelerated providing greater efficiency and further lessening the trauma to the patient. Also, the heat generated to assist in melting some of the fat tends to be focused in the area of the entry orifice(s). The additional heat is generated along the remaining length of the exposed insert 12 thereby providing the relatively thin layer of melted fat. A roughened texture on the insert may provide additional heat generation thereby allowing the surgeon to further fine tune the procedure.

In summary, numerous benefits result from employing the concepts of the present invention. The method herein disclosed reveals a method of liposuction utilizing an ultrasonically vibrating probe 10. The ultrasonic vibrations produce localized tissue separation and heat through frictional contact between the appropriate probe tip 14, 16 or 18 and the fatty tissue. The separated and melted fatty tissue is then emulsified by a localized application of a saline irrigating solution through irrigation sleeve 30. An external suction source is utilized to remove the emulsified solution. Because the procedures as described herein aspirate only the undesired fatty tissue and not blood vessels, muscle tissue and the like, a safer surgical procedure results. The process is also more efficiently carried out in terms of time required to perform the operation since clogging is no longer a problem.

The foregoing description of a preferred embodiment of the invention has been presented for purposes of illustration and description. It is not intended to be exhaustive or to limit the invention to the precise method disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications. All such modifications and variations are within the scope of this invention as determined by the appended claims when interpreted with breadth to which they are fairly, legally and equitably entitled.

We claim:

1. A method of removing animal fatty tissue from a patient in vivo comprising the steps of:
   inserting an aspirating probe into the body in an area between the flesh and the muscle in the area of the fatty tissue;
   ultrasonically vibrating said probe at substantially high frequencies and low amplitudes, creating localized tissue separation and frictional heat;
   melting at least some of said fatty tissue by said localized heat, so as to provide more efficient removal of said fatty tissue;
   irrigating the area surrounding the probe;
   emulsifying said fatty tissue; and
   aspirating the emulsified fatty tissue by applying suction, whereby a slimmer profile is provided.

2. The method of claim 1 wherein adjustment is provided to the amplitude and frequency of said ultrasonic vibrations to vary the intensity of said localized heat.

3. The method of claim 1 wherein placement of said probe is in the area substantially below the patient's blood vessels.

4. The method of claim 1 wherein is provided focusing of said heat adjacent a probe tip having a rounded, closed end and at least one entry orifice.

5. The method of claim 1 wherein is provided focusing of said heat adjacent a probe tip having a rounded, partially closed and partially open end.

6. The method of claim 1 wherein is provided focusing of said heat adjacent the probe tip having a rounded, closed end and multiple in-line orifices.

7. The method of claim 1 including the step of protecting delicate tissue by thermally insulating a portion of said probe tip.

* * * * *